United States Patent [19]

Miyata et al.

[11] Patent Number: 4,824,244
[45] Date of Patent: Apr. 25, 1989

[54] SENSOR FOR MIXING RATIO OF GASOLINE AND ALCOHOL OR THE LIKE

[75] Inventors: Shigeru Miyata; Yoshihiro Matsubara, both of Nagoya, Japan

[73] Assignee: NGK Spark Plug Co., Ltd., Nagoya, Japan

[21] Appl. No.: 54,390

[22] Filed: May 26, 1987

[51] Int. Cl.[4] .......................... F02D 1/00; F02B 3/00; G01N 21/41
[52] U.S. Cl. .................................................. 356/133
[58] Field of Search ................................ 356/133, 128

[56] References Cited

U.S. PATENT DOCUMENTS

| | | | |
|---|---|---|---|
| 4,257,689 | 3/1981 | Yancey | 356/128 |
| 4,438,749 | 3/1984 | Schwippert | 356/133 |
| 4,639,594 | 1/1987 | Schoch et al. | 356/133 |

Primary Examiner—Richard A. Rosenberger
Attorney, Agent, or Firm—Cooper & Dunham

[57] ABSTRACT

A sensor for mixing ratio of liquid fuel comprising: a cylindrical enclosure having both inlet and outlet opening to act as a passage through which a mixing liquid fuel flows; a transparent column concentrically disposed into the enclosure to make outer surface contact with the liquid fuel; light emitting diode and photo diode each provided so as to sandwich the column in the lengthwise direction, so that the light emitted from the former enters the column through its one end and reflects at the boundary of the column and the liquid fuel, and go out of the other end thereof to fall on the latter; a temperature compensation photo diode disposed in the enclosure with the light of the light emitting diode partly as a light source to rectify the characteristics influenced under the ambient temperature variation; a voltage control circuit provided to control the voltage across the light emitting diode so as to maintain uniform output from the temperature compensation photo diode.

2 Claims, 7 Drawing Sheets

Fig.7

SENSOR FOR MIXING RATIO OF GASOLINE AND ALCOHOL OR THE LIKE

BACKGROUND OF THE INVENTION

1. Field of the Invention

This invention relates to a sensor which detects the mixing ratio of gasoline and alcohol or the like employed to as a fuel of internal combustion engine for example.

2. Description of the Prior Art

In recent years, it is planned to extract liquid alcohol from plants. The alcohol thus extracted is mixed with gasoline to use as liquid fuel for internal combustion engine. When employed in an internal combustion engine for motor vehicle, it is necessary to precisely control the mixing ratio of the liquid fuel to obtain maximum output level and avoid adverse effect upon our health due to harmful exhaust gas. This precise control is carried out each time when the liquid fuel changes. When the mixing liquid of gasoline and alcohol is put into market, it is preferably that the mixing liquid is used together with the gasoline.

For this purpose, a transparent column is provided in the condition to make its outer surface contact the mixing liquid fuel of gasoline and alcohol. Light emitting diode and photo diode are arranged to sandwich the column in its lengthwise direction, so that the light emitted from the diode enters the column and reflects at the boundary of the column and the liquid fuel to fall on the photo diode. The change of mixing ratio of the liquid causes a change of the critical angle of the light incident upon the boundary so as to affect the amount of light to which the photo diode is subjected, since the refractive index of the column against the liquid varies depending upon the change of the mixing ratio.

The light emitting diode, however, is subjected to variation according to the ambient temperature, thus it is unable to continuously obtain a precise measurement of a liquid mixing ratio unless a discrete thermal sensor is provided to compensate the output from the photo diode.

Therefore, it is an object of this invention to provide an improved sensor which is capable of continuously measuring a ratio of alcohol and gasoline with high precision irrespective of the ambient temperature in order to obtain the most appropriate timing of ignition and injection when employed to the internal combustion engine by way of example.

According to the present invention, a sensor for the mixing ratio of liquid fuel comprising; a cylindrical enclosure having both inlet and outlet opening to act as a passage through which a mixing liquid fuel flows; a transparent column concentrically disposed in the enclosure to make its outer surface contact with the liquid fuel; light emitting diode and photo diode provided so as to sandwich the column in the lengthwise direction, so that the light emitted from the former enters the column through its one end and reflects at the boundary of the column and the liquid fuel, and go out of the other end thereof to fall on the latter; a temperature compensation photo diode disposed in the enclosure with the light of the light emitting diode partly as a light source to rectify the characteristics influenced under the ambient temperature variation; a voltage control circuit provided to control the voltage across the photo diode so as to maintain uniform output from the temperature compensation photo diode.

DESCRIPTION OF THE PREFERRED EMBODIMENTS

Referring to the drawings the, first embodiment of the invention is described.

Figure 1:
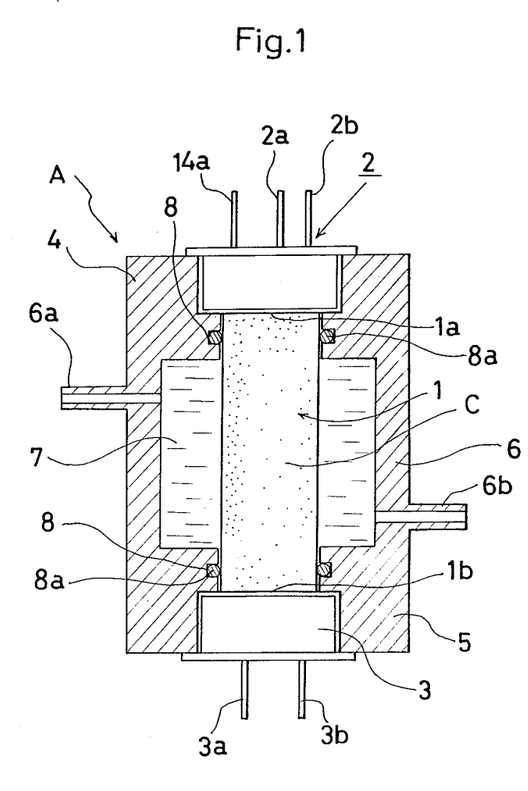
FIG. 1 is a longitudinal cross-section view of a sensor.

Firstly, attention is called to FIG. 1 of the drawings in which longitudinal sectional view of a sensor device is shown. A transparent column 1 which is made of glass, is interfit at each end into a cylindrical grips 4, 5 each of which is made from metal or synthetic resin. Into the grip 4, a light emitting diode 2 is concentrically placed to face the emitting portion 2A against one end 1a of the column 1.

Numerals 2a, 2b designate input terminals of the diode 2. Into the grip 5, a photo diode 3 is concentrically placed to face the light receiving portion against the other end of the column 1. Numerals 3a, 3b designate output terminals of the photo diode 3. Between the grips 4 and 5, a cylindrical casing 6 is interfit to connect therebetween. An annular space is established between the inner surface of the casing 6 and the outer surface of the column 1 to serve as a reservoir 7 to make a mixture liquid in contract with the outer surface of the column 1 at the time of measuring ratio of the liquid mixture. Inlet and outlet couples 6a, 6b are mounted on the casing 6 to be in communication with the inner side of the reservoir 7. Each of the grips 4, 5 has a groove 8a at the inner wall into which a O-ring 8 is interfit to prevent the liquid mixture from leaking between the inner wall and the outer surface of the column 1.

Figure 2:
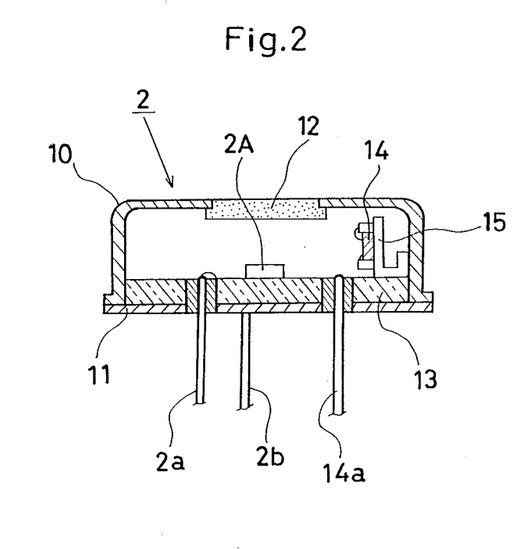
FIG. 2 is a cross-section view looked differently from FIG. 1.

In the meantime, the light emitting diode 2 has an enclosure comprising a lid 10 and a bottom plate 11 each rigidly secured by means of such as, for example, adhesive. On the middle of the plate 11, is a photo diode chip 2A which embodies the light emitting diode 2 through an insulator plate 13. The chip 2A, which serves as a light source of a temperature compensation photo diode 14, positions to be lateral registration with the diode 14 at the outer peripheral of the bottom plate 11 by means of a mounting piece 15. A glass window 12 is provided at the central portion of the lid 10 to look down the chip 2A so as to introduce the light of the chip 2A therethrough. Numerals 2a, 2b designate output and input terminal of the chip 2A, while numeral 14a being an output terminal of the diode 14.

Figure 3:
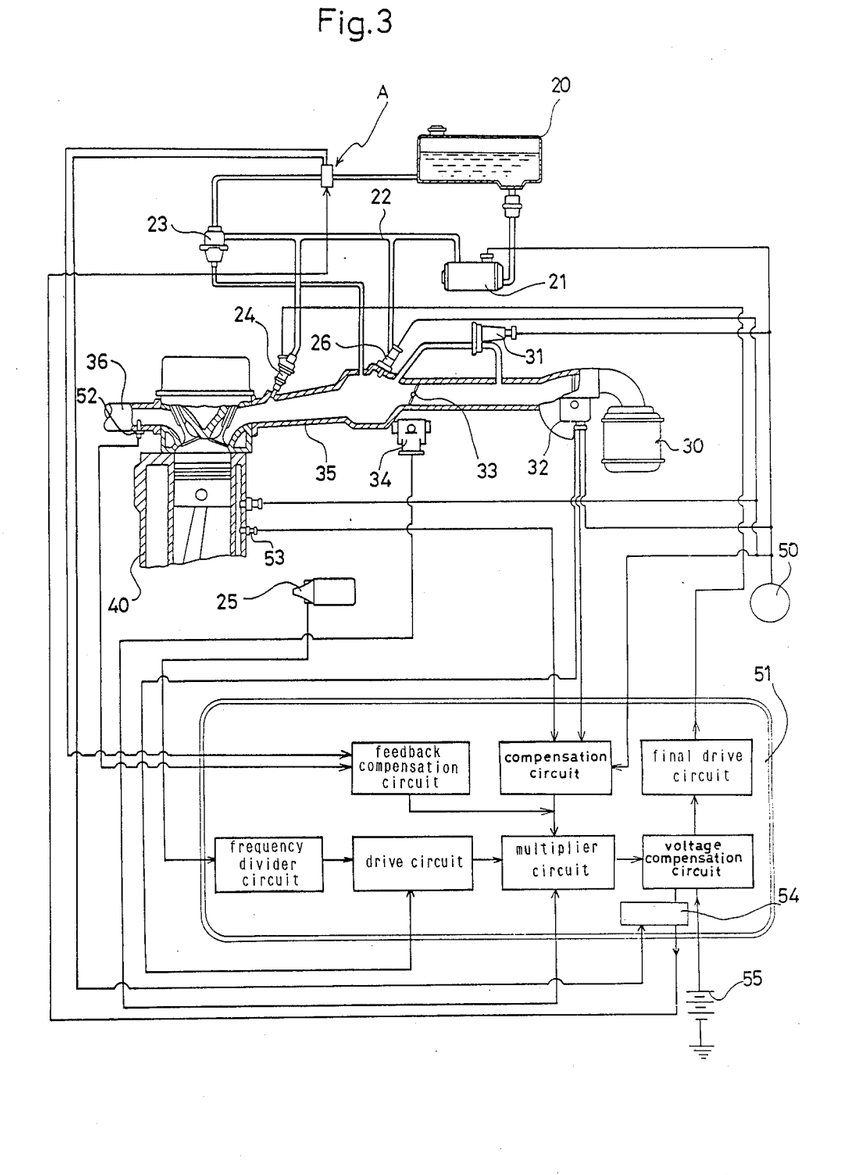
FIG. 3 is a schematic diagram of an electronic fuel injection control device for automobile engine.

FIG. 3 shows a schematic diagram of control system for automobile engine into which electronic control fuel injection is associated. In FIG. 3, numeral 40 shows an engine cylinder, numeral 50 a key switch of the engine, numeral 51 control circuit, numeral 55 an electrical source mounted on the automobile, numeral 20 fuel tank, denotation (A) a sensor which detects a mixture ratio of gasoline and alcohol. Numeral 21 is a fuel pump referred to as a primary constituent of fuel system, numeral 23 a pressure regulator, numeral 24 an injector, numeral 26 a cold start injector, numeral 25 an ignition coil, numeral 30 an air cleaner, numeral 31 an air valve, numeral 32 an air flow meter, numeral 33 a throttle valve, numeral 34 a throttle position sensor, numeral 35 an intake pipe, numeral 36 an exhaust pipe. Numerals 52 and 53 designate an oxgen sensor and a water temperature sensor respectively.

Figure 4:
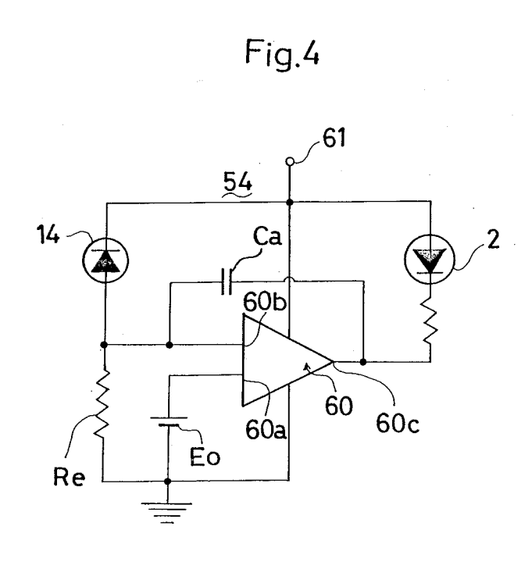
FIG. 4 is a view of an electronic circuit.

In the circuit 54 of FIG. 4, an operation amplifier 60 has an input terminal 60a grounded through a battery E0. Across another input terminal 60b and an output terminal 60c, the light emitting diode 2 and the thermal compensating photo diode 14 which are connected in series each other, are provided. An electrical resistor Re is connected across the common point of the input terminal 60b and the photo diode 14, and the negative pole of the battery E0. A capacitor Ca is connected in parallel with the diode 2 and the thermal compensating diode 14 in order to avoid a hunting. An input terminal 61 is connected to the control circuit 51.

In operation, the key switch 50 is set at the start position to start the engine, and power is supplied to the control circuit 51. On the other hand, the liquid mixture which is the mixture of gasoline and alcohol at the appropriate ratio to serve as a fuel contained in the fuel tank 20, is introduced into the injector 24 by the pump 21 through a fuel pipe 22. The injector 24 injects the best suited amount of the liquid mixture into the intake pipe 35 in accordance with the control circuit 51.

Meanwhile, the sensor A is connected intermediate of the pipe 22 through the couples 6a, 6b. The power is applied to the diode 2 from the control circuit 51 to emit light which falls on one end 1a of the column 1. The light incident on the boundary between the liquid mixture and the column 1, totally reflects and pass through the column 1 to fall on the photo diode 3, if the incident angle is greater than the critical angle. The photo diode 3 thus subjected to the light, is activated to produce an output proportional to the amount of the light across the terminals 3a, 3b.

On the other hand, the light incident upon the boundary the incident angle of which is smaller than the critical angle, refracts at the boundary to escape out of the column 1, and substantially has no affect upon the output of the diode 3. The critical angle at the boundary of the liquid mixture (C), changes depending upon the mixing ratio of gasoline and alcohol (generally referred methyl alcohol), so the light which emits from the diode 2 and reflects at the boundary only once to be caught by the diode 3, changes in its magnitude according to the mixing ratio of gasoline and alcohol.

Consequently, it is obviously possible to reduce the output of the photo diode 3 to the mixing ratio of gasoline and alcohol by the use of an electronic circuit when the relation between the output of the diode and the mixing ratio of gasoline and alcohol is previously obtained through a series of experimentations.

In this instance, the light emitting diode 2 and the photo diode 3 is subjected to variation of its characteristics depending upon the ambient temperature. The ambient temperature variation causes to change the light emitted from the light emitting diode 2 and the amount of the light to which the photo diode 14 is exposed so as to alter its output. The decrease of current flowing through the diode 14 causes to decrease the current flowing through the resistor Re. That is, the current flowing through the diode 14 is compensated by the current increase across the light emitting diode 2, so that the light emitting degree is substantially maintained uniform, irrespective of the ambient temperature variation.

Second embodiment of the invention is described in reference with FIG. 5 through FIG. 8. It has been known that the current supplied to a light emitting diode 135 is required to change depending upon the ambient temperature as seen at (1) in FIG. 6 so as to maintain a uniform output of a photo diode 136. The output of the photo diode 155 is subjected to change as seen at the solid line (m) in FIG. 7 according to the ambient temperature under the condition that the constant mixing ratio of the liquid fuel is maintained.

Figure 5:
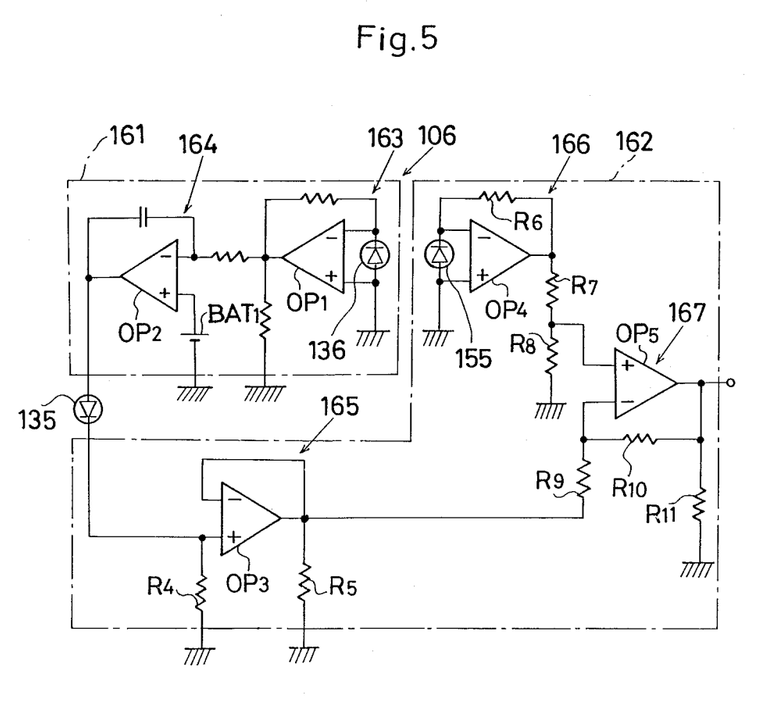
FIG. 5 is an electronic circuit to compensate light emitting diode and photo diode.

An electronic circuit 106 of FIG. 5 has a compensation circuit 161 to control the light emitting degree of the diode 135 so as to maintain uniform output from a compensation photo didoe 136. The circuit 106 further comprises a compensation circuit 162 to make up for the critical angle influenced due to the ambient temperature. In the compensation circuit 161, first light measurement portion 163 which converts the light of the diode 136 into voltage. A control portion 164 applies an output across the diode 135 to make the output of the portion 163 equal to that of a battery BAT1. The first light measurement portion 163 has first operational amplifier OP1 into which the voltage across the diode 136 is inputed. The decreased ambient temperature induces to increase the light emitting degree of the diode 135 so as to enhance the output from the amplifier OP1. The control portion 164 has second operational amplifier OP2 which inputs the output from the first amplifier OP1 and the reference voltage of the battery BAT1. The lowered ambient temperature causes to reduce the voltage to the diode 135 so as to lessen the light emitting degree. While, the elevated ambient temperature causes to increase the voltage to the diode 135 so as to intensify the light emitting degree.

In the meanwhile, the compensation circuit 162 has a voltage follower 165, and second light measurement portion 166 which converts the light of the diode 155 into voltage. A calculation circuit 167 is provided with the circuit 162 to substract the output of the voltage follower 165 from that of the measurement portion 166. The voltage follower 165 has third operational amplifier OP3 and electrical resistors R4, R5 with the output of the diode 135 as an input. The output of the amplifier OP3 is taken as the output of the diode 135 in accordance with the ambient temperature. The second light measurement portion 166 has fourth operational amplifier OP4 which renders voltage difference of the dual terminals as an input, and including electrical resistors R6, R7, R8. The output from the amplifier OP4 increases with the increase of alcohol percentage of the liquid fuel, while decreasing with the increase of the ambient temperature under the condition that uniform ratio of the mixing liquid fuel is maintained.

The calculation circuit 167 has fifth operational amplifier OP5 which inputs the outputs from the third operational amplifier OP3 and the fourth operational amplifier OP4, while generating an output equivalent to the subtraction from the divisional voltage of the amplifier OP4 to the output of the amplifier OP3. The circuit 167 further has resistors R9, R10 and R11, with the result that the calculation circuit 167 generates an output which is compensated for the change of critical angle under the influence of the ambient temperature. Thus, the output voltage from the circuit 167 changes depending upon the mixing ratio of the liquid fuel as shown at solid line (n) in FIG. 8, the relation of which is generally immuned to the influence of the temperature variation of the fuel. Reading the output voltage of FIG. 8 readily allows to measure the mixing ratio of the liquid fuel.

Figure 5A:
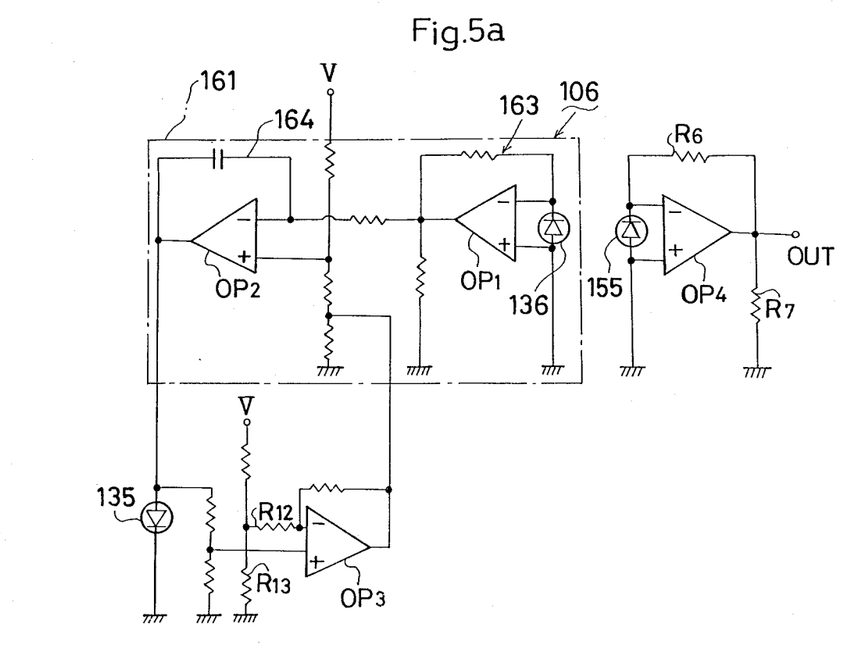
FIG. 5a is a electrical wiring diagram of an electronic circuit.

Now, in reference with FIG. 5a of the drawings, third embodiment of the invention is described below. In this third embodiment, the calculation circuit 167 of the second embodiment is omitted. Instead of the calculation circuit 167, the operational amplifier OP4 makes its output terminal serve as an output of the photo diode 155.

In the meantime, the light emitting diode 135 has its negative polarity grounded, and its positive polarity connected to the plus terminal of the operational amplifier OP3. The output terminal of the amplifier OP3 is connected to the plus terminal of the operational amplifier OP2 instead of the battery BAT1 in the second embodiment. The minus terminal of the amplifier OP3 is grounded through resistors R12, R13.

Figure 5B:
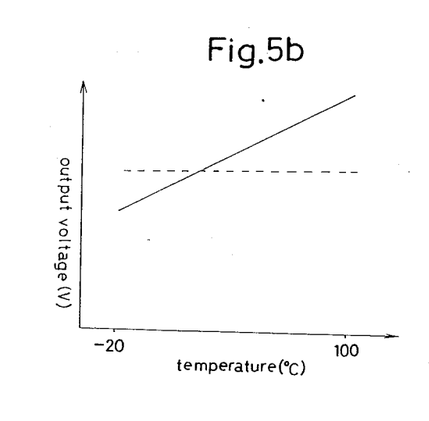
FIG. 5b is a graph showing relationship between output and the temperature.

With the structure of the third embodiment, the output of the amplifier OP4 change under the influence of the ambient temperature which affects on the photo diode 155 in a manner as shown at solid line in FIG. 5b in which the relationship between the output voltage and the temperature is shown, if the battery BAT1 of the second embodiment remains.

Figure 5C:
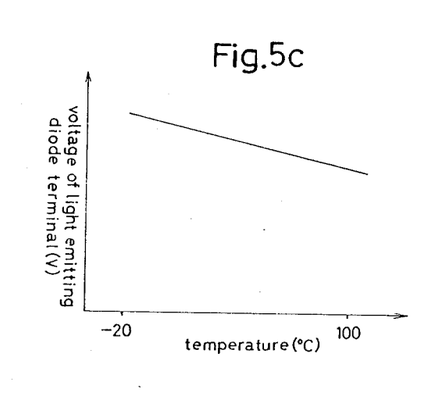
FIG. 5c is a graph showing relationship between light emitting diode terminal voltage and the temperature.
Figure 5D:
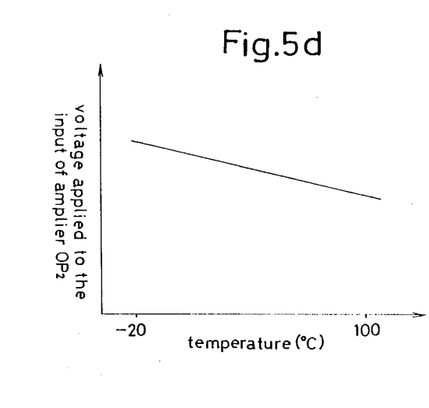
FIG. 5d is a graph showing relationship between voltage and the temperature.
Figure 6:
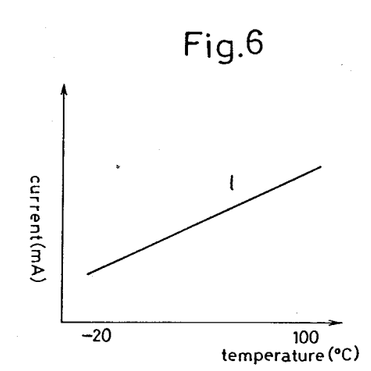
FIG. 6 is a graph showing a relationship between the ambient temperature and current to be supplied.
Figure 7:
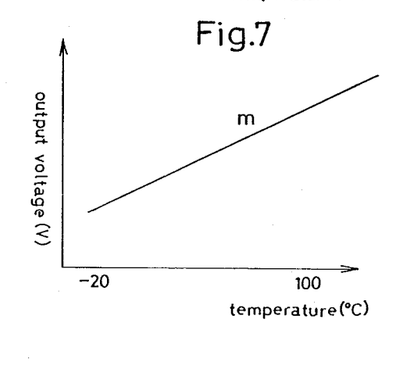
FIG. 7 is a graph showing a relationship between the temperature and the output of a photo diode.
Figure 8:
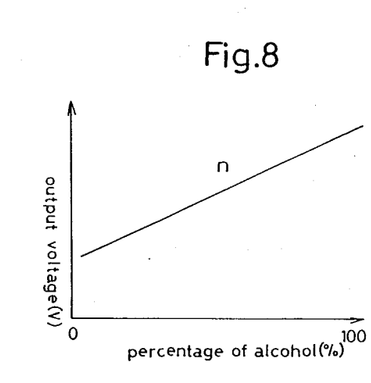
FIG. 8 is a graph showing a relationship between the mixing ratio of liquid fuel and the output.

Meanwhile, the light emitting diode 135 lowers the voltage across its terminals in reverse proportion with the temperature as shown in FIG. 5c in which the relationship between the light emitting diodie terminal voltage and the temperature is depicted. The terminal voltage of the diode 135 as shown in FIG. 5c is fed into the amplifier OP3 through the plus terminal, and generate an output through the output terminal as seen in FIG. 5d in which decreses the voltage with the increase of the ambient temperature. As a consequence, progressively decreasing voltage is impressed across the diode 135 through the output terminal of the amplifier OP2 with the rise of ambient temperature. As a result, the quantity of the light emitted from the diode 135 reduces to lessen the output of the photo diode 155 in a manner as seen at dotted line in FIG. 5b in which the constant output is maintained irrespective of the ambient temperature variation.

In this third embodiment, like references designate like parts all through the drawings.

It is appreciated that instead of gasoline, other fosil fuel such as light oil, gas oil of kerosine may be employed.

It is also noted that the outer peripheral surface of the column is partly in contact with the liquid fuel.

What is claimed is:

1. A sensor for determining mixing ratio of liquid fuel comprising:
    a cylindrical enclosure (6) having both inlet and outlet openings to act as a passage through which a mixing liquid flows:
    a transparent column (1) concentrically disposed in said enclosure to provide an outer surface thereof at least partially in contact with said mixing liquid fuel;
    a light emitting diode (135) placed at one end of said column so that light beams emanated from said diode enter into said column to reach the boundary of said column and said mixing liquid fuel, said plight beams incident on said boundary at an angle of less than a critical angle being passed beyond said boundary to said mixing liquid fuel, while said light beams incident on said boundary at an angle greater that said critical angle are totally reflected back at said boundary;
    a photo diode (155) placed at the other end of said column (1) to receive said light beams totally reflected back at said boundary so as to produce an output, the intensity of which is in accordance with a ratio of said mixing liquid fuel;
    the improvement being a temperature compensation means comprising:
    first light measurement portion (163) having a compensation photo diode (136) across both terminals of which an amplifier (OP1) is connected;
    second light measurement portion (166) having an amplifier (OP4) connected across said photo diode (155) to produce an output in proportion with an increase of alcohol component of said mixing liquid;
    a control portion (164) having an amplifier (OP2) through which an output of said amplifier (OP1) is fed to said light emitting diode (135) in a manner to maintain a constant intensity of light beams from said diode (135) by controlling current flowing therethrough so as to regulate an output variation of said photo diode (136) under changing ambient temperature;
    a voltage follower (165) having an amplifier (OP3) positive input terminal which receives an output of said light emitting diode (135) while the negative terminal of which is connected to an output terminal of said amplifier (OP3) and grounded by way of electrical resistance;
    a calculation circuit (167) having an amplifier (OP5) one input terminal of which receives the output of said voltage follower (165) while other input terminal of which receives the output of said amplifier (OP4) to produce an output corresponding to subtraction between the output of said voltage follower (165) and the output of said amplifier (OP4) thereby correcting the measured refraction index under changing ambient temperature.

2. A sensor for determining mixing ratio of liquid fuel comprising:
    a cylindrical enclosure (6) having both inlet and outlet openings to act as a passage through which a mixing liquid flows;
    a transparent column (1) concentrically disposed in said enclosure to make an outer surface at least partially in contact with said mixing liquid fuel;
    a light emitting diode (135) placed at one end of said column so that light beams emanated from said diode enter into said column to reach the boundary of said column and said mixing liquid fuel, said light beams incident on said boundary at an angle of less than a critical angle being passed beyond said boundary to said mixing liquid fuel, while said light beams incident on said boundary at an angle greater than said critical angle being totally reflected back at said boundary;

a photo diode (155) placed at the other end of said column (1) to receive said light beams totally reflected back at said boundary so as to produce an output, the intensity of which is in accordance with the ratio of said mixing liquid fuel;

the improvement being a temperature compensation means comprising:

first light measurment portion (163) having a compensation photo diode (136) across both terminals of which an amplifier (OP1) is connected;

an amplifier (OP4) connected across said photo diode (155) to produce an output in proportion to the increase of alcohol component of said mixing liquid;

a control portion (164) having an amplifier (OP2) the negative terminal of which the output terminal of said amplifier (OP1) is connected while the output terminal of said amplifier (OP2) is connected to one end of said light emitting diode (135) the other end of which is grounded;

an amplifier (OP3) having a positive terminal connected to a common point between said amplifier (OP2) and said light emitting diode (135) and having a negative terminal grounded and having an output terminal connected to the positive terminal of said amplifier (OP2); whereby said compensation photo diode (136) serves to control current flowing through said light emitting diode (135) by way of said amplifiers (OP1) and (OP2) so as to maintain intensity of light beams emanated therefrom and correcting temperature dependency of the diode (135) under changing ambient temperature while the current controlled by said compensation photo diode (136) is fed to said light emitting diode (135) through said amplifiers (OP3) and (OP2) to correct the measured refraction index.

* * * * *